(12) United States Patent
Zdeblick

(10) Patent No.: US 7,877,149 B2
(45) Date of Patent: *Jan. 25, 2011

(54) ELECTRICAL ANGLE GAUGE

(75) Inventor: Mark Zdeblick, Portola Valley, CA (US)

(73) Assignee: Proteus Biomedical Inc., Redwood City, CA (US)

( * ) Notice: Subject to any disclaimer, the term of this patent is extended or adjusted under 35 U.S.C. 154(b) by 870 days.

This patent is subject to a terminal disclaimer.

(21) Appl. No.: 11/555,178

(22) Filed: Oct. 31, 2006

(65) Prior Publication Data

US 2007/0123944 A1     May 31, 2007

Related U.S. Application Data

(63) Continuation-in-part of application No. PCT/US2005/046811, filed on Dec. 22, 2005, which is a continuation-in-part of application No. PCT/US2005/031559, filed on Sep. 1, 2005.

(60) Provisional application No. 60/732,417, filed on Oct. 31, 2005, provisional application No. 60/638,692, filed on Dec. 22, 2004, provisional application No. 60/655,609, filed on Feb. 22, 2005, provisional application No. 60/751,111, filed on Dec. 15, 2005, provisional application No. 60/752,733, filed on Dec. 20, 2005, provisional application No. 60/607,280, filed on Sep. 2, 2004, provisional application No. 60/638,928, filed on Dec. 23, 2004, provisional application No. 60/679,625, filed on May 9, 2005, provisional application No. 60/707,995, filed on Aug. 12, 2005.

(51) Int. Cl.
*A61N 1/00* (2006.01)

(52) U.S. Cl. .................................................. 607/62
(58) Field of Classification Search ............... 607/2, 607/19, 62, 115, 119; 600/374, 509
See application file for complete search history.

(56) References Cited

U.S. PATENT DOCUMENTS

| 4,182,315 | A | * | 1/1980 | Vas et al. ................... 600/500 |
|---|---|---|---|---|
| 5,628,777 | A | * | 5/1997 | Moberg et al. ............. 607/122 |
| 5,662,108 | A | * | 9/1997 | Budd et al. ................. 600/374 |
| 5,772,108 | A | | 6/1998 | Ruggiere, Sr. et al. |
| 5,983,126 | A | | 11/1999 | Wittkampf |
| 2003/0065365 | A1 | | 4/2003 | Zhu et al. |
| 2004/0193021 | A1 | | 9/2004 | Zdeblick et al. |
| 2005/0038481 | A1 | | 2/2005 | Chinchoy et al. |
| 2008/0058656 | A1 | * | 3/2008 | Costello et al. ............. 600/508 |

FOREIGN PATENT DOCUMENTS

| WO | WO2006029090 A2 | 3/2006 |
|---|---|---|
| WO | WO2006042039 A2 | 4/2006 |
| WO | WO2006069322 A2 | 6/2006 |

* cited by examiner

*Primary Examiner*—George Manuel
*Assistant Examiner*—Shubatra Narayanaswamy
(74) *Attorney, Agent, or Firm*—Bret E. Field; Bozicevic, Field & Francis LLP

(57) ABSTRACT

Methods of using electrodes to obtain physiological location motion data are provided. Embodiments of the methods include producing an electrode from a broadcasting electrode that is proximal to the physiological location of interest and detecting a change in an induced electric potential at a receiving electrode to obtain the motion data of interest. Also provided are systems and components thereof, e.g., programming, for practicing methods according to embodiments of the invention.

17 Claims, 8 Drawing Sheets

Satellite 2

Satellite 4

ELECTRICAL ANGLE GAUGE

CROSS-REFERENCE TO RELATED APPLICATIONS

This application claims priority to: United States Provisional Application Ser. No. 60/732,417 filed on Oct. 31, 2005; United States Application Serial No. US2005/046811 filed Dec. 22, 2005 and United States Application Serial No. US2005/031559 filed Sep. 1, 2005; the disclosures of which priority applications are herein incorporated by reference.

INTRODUCTION

1. Field of the Invention

The present invention relates generally to medical apparatus and methods. More specifically, the present invention relates to apparatus and methods for measuring cardiac motion or the position of a pacing lead using electrical angle gauges. The methods, apparatus, and systems described herein facilitate optimization of cardiac resynchronization intervention, arrhythmia management, ischemia ejection, coronary artery disease management, and heart failure management.

2. Background

Cardiac Resynchronization Therapy (CRT) is a promising approach to treating cardiac conditions. Typically, CRT involves implanting various medical devices, such as pacing electrodes, into a patient's heart. For example, a physician stimulates the heart through the pacing electrode, and adjusts the timing of the pacing signals in an attempt to improve the timing of the heart's contraction. The physician generally does not have sufficient knowledge of the pacing device's exact location. The result of such therapy is often based on empirical data.

Current systems provide cardiac pacing on an empiric basis. Ultrasonic approaches have been proposed to quantitatively improve the synchronization procedure. Such procedures, however, are time-consuming and costly because external cardiac ultrasound is required. A physician typically attempts to visualize cardiac wall motion with the aid of an ultrasonic machine and calculates a synchronicity index. Nevertheless, ultrasonic equipment may not always be available and the operation thereof requires special training.

Hence, there is an acute need for an apparatus and a method for effectively measuring cardiac wall movements with reduced footprint and ease of operation.

SUMMARY

The present invention relates to apparatus and methods for measuring cardiac motion or the position of a pacing lead using electrical angle gauges. The methods, apparatus, and systems described herein facilitate optimization of cardiac resynchronization intervention, arrhythmia management, ischemia ejection, coronary artery disease management, and heart failure management.

DETAILED DESCRIPTION

As summarized above, the present invention relates to apparatus and methods for measuring cardiac motion or the position of a pacing lead using electrical angle gauges. The methods, apparatus, and systems described herein facilitate optimization of cardiac resynchronization intervention, arrhythmia management, ischemia ejection, coronary artery disease management, and heart failure management.

Motion Detection Systems that Include Electrical Angle Gauges

One embodiment of the present invention provides a cardiac motion detection system which includes a number of electrical angle gauges coupled to a single lead. In certain embodiments, systems of the invention include: a housing which includes a power source and an electrical stimulus control element; and one or more vascular leads as described above, e.g., 2 or more vascular leads, where each lead is coupled to the control element in the housing via a suitable connector, e.g., an IS-1 connector. In certain embodiments, the systems are ones that are employed for cardiovascular applications, e.g., pacing applications, cardiac resynchronization therapy applications, etc. As such, in certain embodiments the control element is configured to operate the pulse generator in a manner so that it operates as a pacemaker, e.g., by having an appropriate control algorithm recorded onto a computer readable medium of a processor of the control element. In certain embodiments the control element is configured to operate the pulse generator in a manner so that it operates as a cardiac resynchronization therapy device, e.g., by having an appropriate control algorithm recorded onto a computer readable medium of a processor of the control element.

Figure 1A:
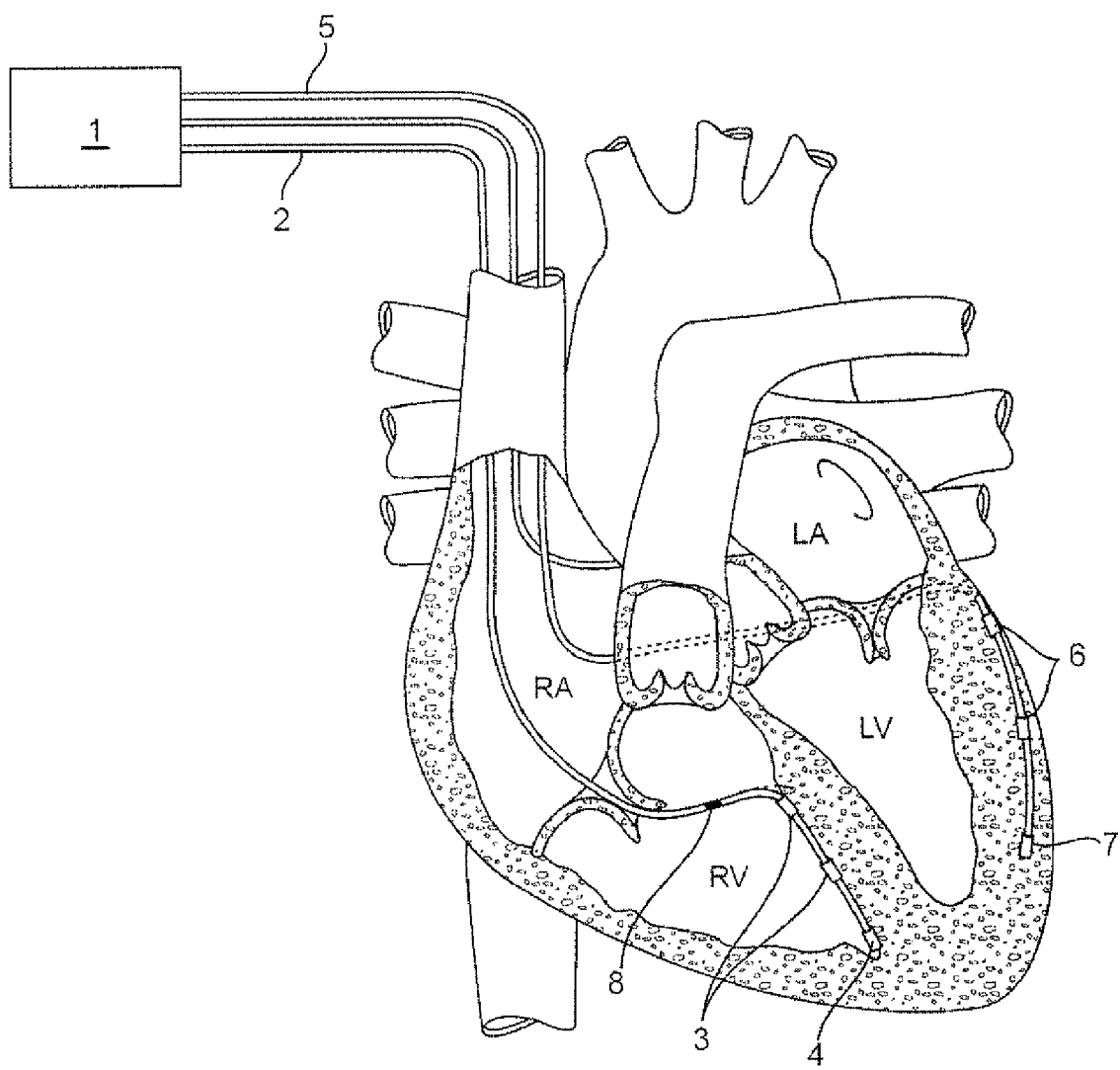
FIG. 1A illustrates the location of a number of electrical angle gauges in accordance with an embodiment of the present invention.

FIG. 1A illustrates the location of a number of electrical angle gauges in accordance with an embodiment of the present invention. Communication means 1 provides the extra-cardiac communication, signal transmission, and signal collection means for the overall system. In more complex configurations, communication means 1 may provide a means for communicating data and driving voltage from a completely external or extracorporeal location.

Right ventricular lead 2 emerges from the communication device in communication means 1, and travels from the preferentially subcutaneous location of communication means 1 via the subclavian venous access through the superior vena cava and the right atrium, and then through the tricuspid valve to a position along the right ventricle. This location is preferentially located along its distal portion in close association with the intraventricular septum terminating distally with fixation in the right ventricular apex.

Particular to distal aspect of right ventricular lead 2 are electrical angle gauges 3 and 4. In further embodiments of the present invention, a larger number or smaller number of electrical angle gauges may be employed.

Additionally, emerging at the proximal aspect of communication means 1 is left ventricular lead 5. Left ventricular lead 5 starts by following the same route as right ventricular lead 2 via subclavian vein through the superior vena cava into the right atrium. At this point, left ventricular lead 5 is placed via the coronary sinus around the posterior aspect of the heart and into cardiac vein draining into said sinus.

FIG. 1A further depicts left ventricular lead 5 in a position likely to be advantageous for biventricular pacing located along the lateral aspect of the left ventricle. Electrical angle gauges 6 and 7 in the left ventricular are analogous to gauges 3 and 4 which are previously described.

Figure 1B:
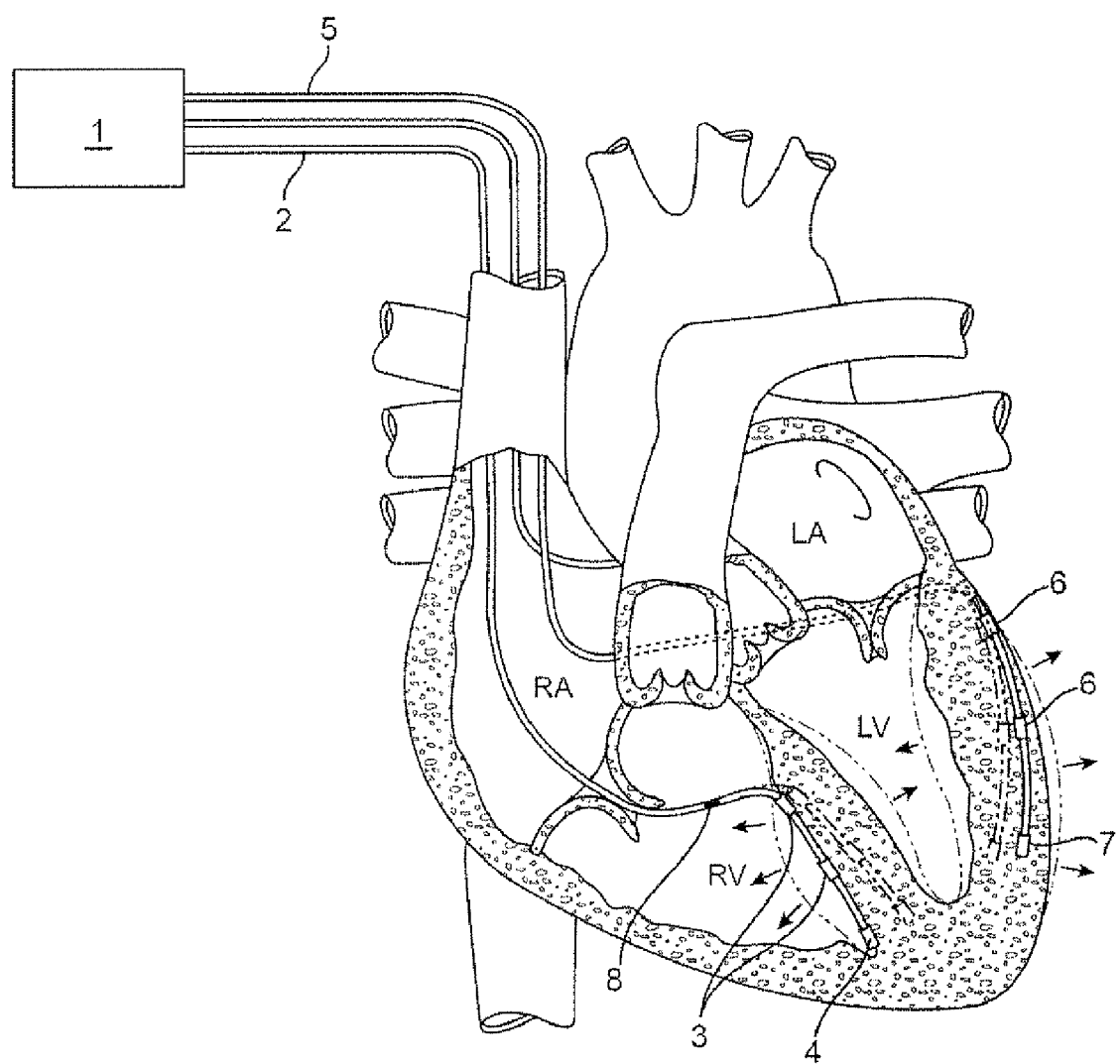
FIG. 1B illustrates the location of a number of electrical angle gauges showing additionally the cardiac motion in accordance with an embodiment of the present invention.

Right ventricular lead 2 may optionally be provided with pressure sensor 8 which is located in the right ventricle. Pressure sensor 8 provides a pressure signal which can also simultaneously be obtained with wall motion data. Adding active devices such as pressure sensor 8 to said lead can be facilitated through the use of a multiplexing system FIG. 1B illustrates the location of a number of electrical angle gauges showing additionally the cardiac motion in accordance with an embodiment of the present invention. Right ventricular lead 2 and left ventricular lead 5 are provided in close association with the wall of the heart. As the wall of the heart moves through a cardiac cycle, so do the leads (i.e., catheters) in a proportionate amount. As these catheters bend at certain locations in response to the cardiac contractions, the electrical angle gauges detect the corresponding amount of bending along the lead which varies over the course of the cardiac cycle. This variation indicates the movement and the timing thereof at various locations.

The cardiac motion data, together with an optional pressure signal or other auxiliary signals, is used to optimize the CRT. The goal of the treatment is to maximize the contractility of the left ventricle based on simultaneous contraction of the bulk of the muscle of the left ventricle. In many congestive heart failure patients, such contractility is impaired with dyskinetic contraction, which typically occurs with a septal contraction against a relaxed left ventricle followed by ventricular contraction against a relaxing septum. The result is inefficiency with regards to the blood being moved around the ventricle rather than constrictively expelled from the ventricle as in a normal case.

One embodiment of the present invention provides a cardiac motion detection system for measuring cardiac motion in real time and in a numeric format useable by both the physician and by an automated pacing system. An electric angle gauge, according to one embodiment, detects abnormalities in wall motion associated with ischemia or arrhythmia and other cardiac abnormalities, including progression of underlying disease states such as congestive heart failure. If coupled to an external or fully implanted real-time monitoring system, such abnormalities can trigger an alarm. This alarm alerts the patient or a physician of the advent of these abnormalities.

In one embodiment of the present invention, a control module of the system is coupled to two bus wires residing within a cardiac pacing lead. Along the pacing lead, a number of pacing satellites are coupled to the two bus wires. Each satellite includes a number of electrodes, which can transmit or receive electrical signals. As explained in subsequent sections, two electrodes within a satellite are selected and used as broadcasting electrodes. The broadcasting electrodes transmit an alternating-current (AC) signal to the receiving electrodes. Consequently, the broadcasting electrodes establish an AC field in the nearby region.

Being in this AC field, a neighboring satellite detects a voltage signal on one of the electrodes thereof. The detected voltage signal varies with the angle between the axes of the broadcasting satellite and the detecting satellite In this way, the system can measure the amount of bending along the pacing lead between two neighboring satellites. If the lead is attached to the cardiac wall and moves with cardiac motions, the system can then determine the timing of the cardiac motion.

As such, embodiments of the invention include medical carriers that include one or more electrode satellite structures. Carriers of interest include, but are not limited to, vascular lead structures, where such structures are generally dimensioned to be implantable and are fabricated from a physiologically compatible material. With respect to vascular leads, a variety of different vascular lead configurations may be employed, where the vascular lead in certain embodiments is an elongated tubular, e.g., cylindrical, structure having a proximal and distal end. The proximal end may include a connector element, e.g., an IS-1 connector, for connecting to a control unit, e.g., present in a "can" or analogous device. The lead may include one or more lumens, e.g., for use with a guide wire, for housing one or more conductive elements, e.g., wires, etc. The distal end may include a variety of different features as desired, e.g., a securing means, a particular configuration, e.g., S-bend, etc.

In certain embodiments of the subject systems, one or more sets of electrode satellites is electrically coupled to at least one elongated conductive member, e.g., an elongated conductive member present in a lead, such as a cardiovascular lead. In certain embodiments, the elongated conductive member is part of a multiplex lead. Multiplex lead structures may include 2 or more satellites, such as 3 or more, 4 or more, 5 or more, 10 or more, 15 or more, 20 or more, etc. as desired, where in certain embodiments multiplex leads have a fewer number of conductive members than satellites. In certain embodiments, the multiplex leads include 3 or fewer wires, such as only 2 wires or only 1 wire. Multiplex lead structures of interest include those described in application Ser. No. 10/734,490 titled "Method and System for Monitoring and Treating Hemodynamic Parameters" filed on Dec. 11, 2003; PCT/US2005/031559 titled "Methods and Apparatus for Tissue Activation and Monitoring," filed on Sep. 1, 2006; PCT/US2005/46811 titled "Implantable Addressable Segmented Electrodes" filed on Dec. 22, 2005; PCT/US2005/46815 titled "Implantable Hermetically Sealed Structures" filed on Dec. 22, 2005; 60/793,295 titled "High Phrenic, Low Pacing Capture Threshold Implantable Addressable Segmented Electrodes" filed on Apr. 18, 2006 and 60/807,289 titled "High Phrenic, Low Capture Threshold Pacing Devices and Methods," filed Jul. 13, 2006; the disclosures of the various multiplex lead structures of these applications being herein incorporated by reference. In some embodiments of the invention, the devices and systems may include onboard logic circuitry or a processor, e.g., present in a central control unit, such as a pacemaker can. In these embodiments, the central control unit may be electrically coupled to the lead by a connector, such as a proximal end IS-1 connection.

The satellite structures of the systems of the invention may vary. In certain embodiments, the satellite structures may include control circuitry, e.g., in the form of an IC (e.g., an IC inside of the support), such that the satellite structure is addressable. In certain embodiments, the structure includes two or more electrode elements, such as three or more electrode elements, including four or more electrode elements, e.g., where the structure is a segmented electrode structure.

In certain embodiments, the satellites are segmented electrode structures. By segmented electrode structure is meant an electrode structure that includes two or more, e.g., three or more, including four or more, disparate electrode elements. Embodiments of segmented electrode structures are disclosed in Application Serial No.: PCT/US2005/031559 titled "Methods and Apparatus for Tissue Activation and Monitoring," filed on Sep. 1, 2006; PCT/US2005/46811 titled "Implantable Addressable Segmented Electrodes" filed on Dec. 22, 2005; PCT/US2005/46815 titled "Implantable Hermetically Sealed Structures" filed on Dec. 22, 2005; 60/793, 295 titled "High Phrenic, Low Pacing Capture Threshold Implantable Addressable Segmented Electrodes" filed on Apr. 18, 2006 and 60/807,289 titled "High Phrenic, Low Capture Threshold Pacing Devices and Methods," filed Jul. 13, 2006; the disclosures of the various segmented electrode structures of these applications being herein incorporated by reference. In these embodiments, the satellite may include may include 2 or more, 3 or more, 4 or more, etc., electrode elements, where structures that include four different electrodes may be referred to as quadrant electrodes.

In certain embodiments, the satellites are addressable. Addressable electrode structures include structures having one or more electrode elements directly coupled to control circuitry, e.g., present on an integrated circuit (IC). Addressable electrode structures include satellite structures that include one more electrode elements directly coupled to an IC and configured to be placed along a lead. Examples of addressable electrode structures that include an IC are disclosed in application Ser. No. 10/734,490 titled "Method and System for Monitoring and Treating Hemodynamic Parameters" filed on Dec. 11, 2003; PCT/US2005/031559 titled "Methods and Apparatus for Tissue Activation and Monitoring," filed on Sep. 1, 2006; PCT/US2005/46811 titled "Implantable Addressable Segmented Electrodes" filed on Dec. 22, 2005; PCT/US2005/46815 titled "Implantable Hermetically Sealed Structures" filed on Dec. 22, 2005; 60/793,295 titled "High Phrenic, Low Pacing Capture Threshold Implantable Addressable Segmented Electrodes" filed on Apr. 18, 2006 and 60/807,289 titled "High Phrenic, Low Capture Threshold Pacing Devices and Methods," filed Jul. 13, 2006; the disclosures of the various addressable electrode structures of these applications being herein incorporated by reference.

In certain embodiments, the systems of the invention are implantable medical devices. By implantable medical device is meant a device that is configured to be positioned on or in a living body, where in certain embodiments the implantable medical device is configured to be implanted in a living body. Embodiments of the implantable devices are configured to maintain functionality when present in a physiological environment, including a high salt, high humidity environment found inside of a body, for 2 or more days, such as about 1 week or longer, about 4 weeks or longer, about 6 months or longer, about 1 year or longer, e.g., about 5 years or longer. In certain embodiments, the implantable devices are configured to maintain functionality when implanted at a physiological site for a period ranging from about 1 to about 80 years or longer, such as from about 5 to about 70 years or longer, and including for a period ranging from about 10 to about 50 years or longer. The dimensions of the implantable medical devices of the invention may vary. However, because the implantable medical devices are implantable, the dimensions of certain embodiments of the devices are not so big such that the device cannot be positioned in an adult human.

The systems and leads thereof may further include a variety of different effector element, which elements may employ the satellites or structures distinct from the satellites. The effectors may be intended for collecting data, such as but not limited to pressure data, volume data, dimension data, temperature data, oxygen or carbon dioxide concentration data, hematocrit data, electrical conductivity data, electrical potential data, pH data, chemical data, blood flow rate data, thermal conductivity data, optical property data, cross-sectional area data, viscosity data, radiation data and the like. As such, the effectors may be sensors, e.g., temperature sensors, accelerometers, ultrasound transmitters or receivers, voltage sensors, potential sensors, current sensors, etc. Alternatively, the effectors may be intended for actuation or intervention, such as providing an electrical current or voltage, setting an electrical potential, heating a substance or area, inducing a pressure change, releasing or capturing a material or substance, emitting light, emitting sonic or ultrasound energy, emitting radiation and the like.

Effectors of interest include, but are not limited to, those effectors described in the following applications by at least some of the inventors of the present application: U.S. patent application Ser. No. 10/734,490 published as 20040193021 titled: "Method And System For Monitoring And Treating Hemodynamic Parameters"; U.S. patent application Ser. No. 11/219,305 published as 20060058588 titled: "Methods And Apparatus For Tissue Activation And Monitoring"; International Application No. PCT/US2005/046815 titled: "Implantable Addressable Segmented Electrodes"; U.S. patent application Ser. No. 11/324,196 titled"Implantable Accelerometer-Based Cardiac Wall Position Detector"; U.S. patent application Ser. No. 10/764,429, entitled "Method and Apparatus for Enhancing Cardiac Pacing," U.S. patent application Ser. No. 10/764,127, entitled "Methods and Systems for Measuring Cardiac Parameters," U.S. patent application Ser. No. 10/764,125, entitled "Method and System for Remote Hemodynamic Monitoring"; International Application No. PCT/US2005/046815 titled: "Implantable Hermetically Sealed Structures"; U.S. application Ser. No. 11/368, 259 titled: "Fiberoptic Tissue Motion Sensor"; International Application No. PCT/US2004/041430 titled: "Implantable Pressure Sensors"; U.S. patent application Ser. No. 11/249, 152 entitled "Implantable Doppler Tomography System," and claiming priority to: U.S. Provisional Patent Application No. 60/617,618; International Application Serial No. PCT/US05/ 39535 titled "Cardiac Motion Characterization by Strain Gauge". These applications are incorporated in their entirety by reference herein.

Design and Mode of Operation of Electrical Angle Gauge

Figure 2A:
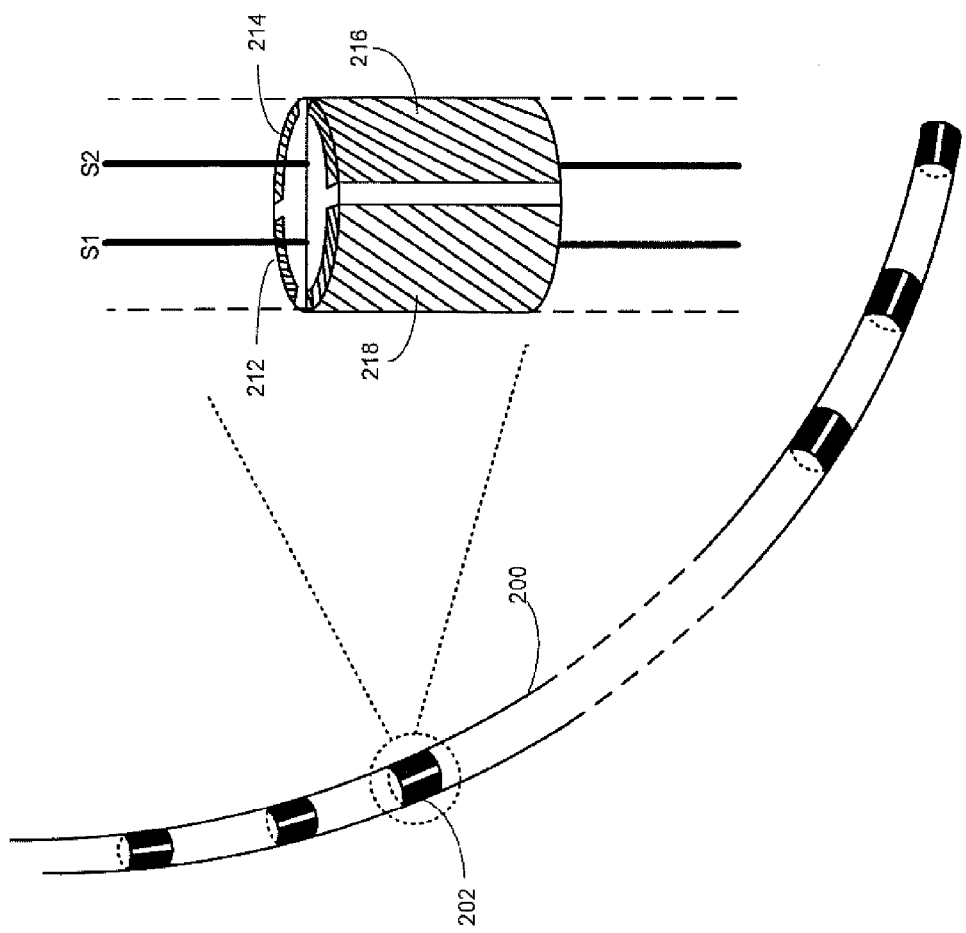
FIG. 2A illustrates an exemplary external view of a number of pacing satellites operating as electrical angle gauges in accordance with an embodiment of the present invention.

One embodiment of the present invention provides a cardiac motion detection system involving two bus wires coupled to one or more pacing satellites. FIG. 2A illustrates an exemplary external view of pacing satellites operating as electrical angle gauges in accordance with an embodiment of the present invention. Pacing lead 200 accommodates a number of pacing satellites, such as satellite 202. As shown in the zoom-in view of satellite 202, there are four electrodes, namely electrodes 212, 214, 216, and 218, situated in the four quadrants of the cylindrical satellite. As such, satellite 202 may be referred to as a "quadrant" electrode. Each satellite is coupled to the two bus wires denoted as S1 and S2.

A satellite also contains a control chip which communicates with an external pacing/signal-detection system and determines which electrodes are coupled to S1 or S2. The configuration of each satellite, the subsequent transmission of AC signals, and the collection of signals from a detecting satellite are all performed over S1 and S2. This configuration is particularly useful because it uses only two wires to perform both downstream and upstream communications.

During operation, the pacing system selects a satellite as a broadcasting satellite. The system transmits an AC signal to a pair of opposite-facing electrodes on the broadcasting satellite. The resulting AC electric field extends to the neighboring satellites near the broadcasting satellite and induces a voltage signal on the electrodes on the neighboring satellite. By measuring the induced voltage on a selected electrode of the detecting satellite, the system can determine the amount and direction of bending incurred to the detecting satellite.

Figure 3:
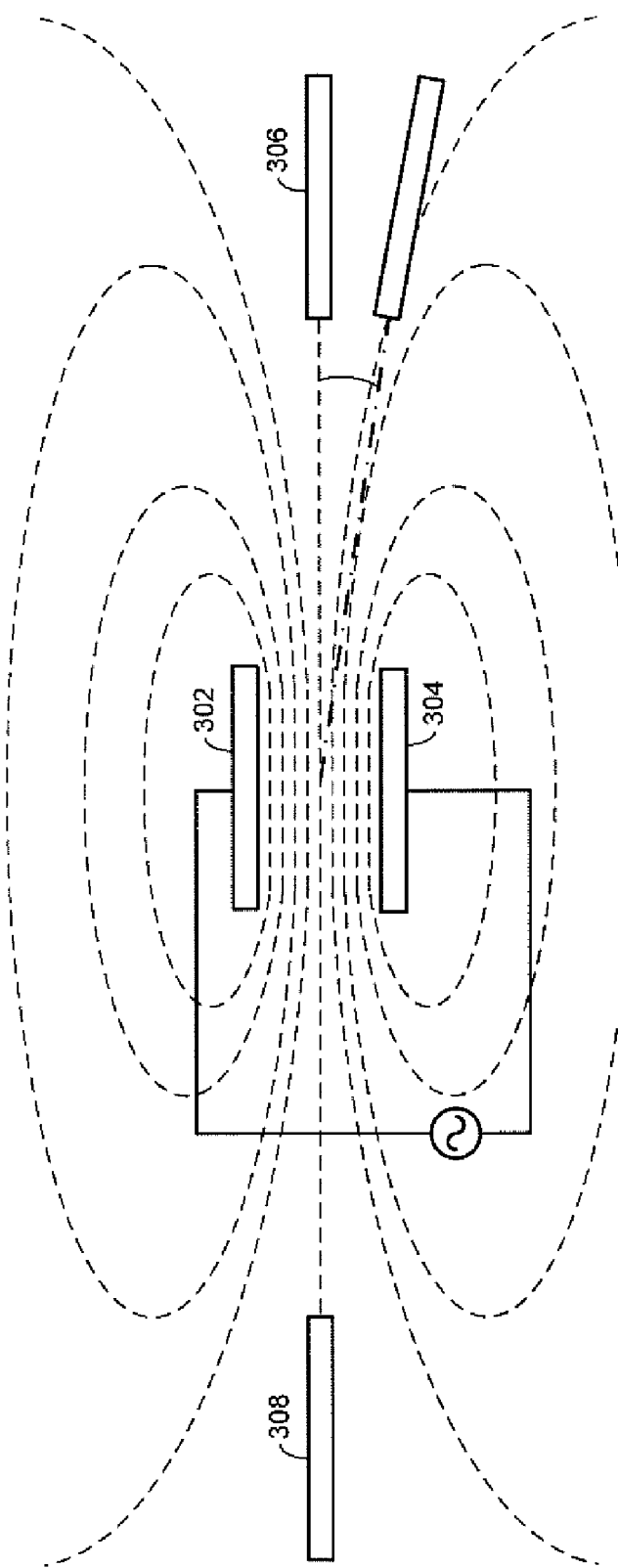
FIG. 3 illustrates an exemplary mode of operation for an electrical angle gauge in accordance with an embodiment of the present invention.

FIG. 3 illustrates an exemplary mode of operation for an electrical angle gauge in accordance with an embodiment of the present invention. A pair of electrodes 302 and 304 on the broadcasting satellite are driven with an AC signal. In one embodiment, this AC signal is transmitted over the bus wires S1 and S2. As a result, an AC electric field is present around electrodes 302 and 304. FIG. 3 illustrates the equipotential lines, shown in dashed lines, of the electrical field. The potential within the middle plane between electrodes 302 and 304 is constant and is at the mid-point between the potential on electrode 304 and the potential on electrode 302.

The electric field sourcing from the electrodes 302 and 304 extends to the electrodes on neighboring satellites, such as electrodes 306 and 308. Consequently, an electrical potential is induced upon electrodes 306 and 308. For example, if electrode 306 is positioned along the mid-potential plane extending between electrodes 302 and 304, the electric potential induced upon electrode 306 is also at a mid-point between the potential on electrode 302 and the potential on electrode 304. If the pacing lead bends toward electrode 304, which results in electrode 306 bending toward electrode 304, the potential induced upon electrode 306 is closer to the potential on electrode 304. Therefore, by detecting the amount of change in the electric potential, which can be detected as voltage, the system can determine the angle θ by which electrode 306 deflects from the mid-potential plane between electrode 302 and 304.

In the illustrated example, the deflection angle θ indicates the amount of bending in a direction orthogonal to the mid-potential plane between electrodes 302 and 304. The system can also use the other two electrodes on the same broadcasting satellite, which results in a mid-potential plane that is parallel to the paper plane and orthogonal to the previous mid-potential plane. In this way, the system can measure a satellite's deflection angle in two orthogonal directions by broadcasting through two pairs of opposite-facing electrodes on a satellite, assuming that the satellite includes four electrodes in four quadrants.

To perform the aforementioned functions, the system first specifies which satellite is to broadcast and which satellite is to detect the induced voltage. Additionally, the system specifies which electrodes on the broadcasting satellite are to be operative, and through which electrode on the receiving satellite the voltage is to be measured. To configure the satellites, the system broadcasts a number of addresses and control commands over S1 and S2 to each satellite. In response, a selected satellite stores the configuration information in its registers and prepares its electrodes for the subsequent transmission or signal collection.

After the selected satellites are activated and the specified electrodes are ready to operate, the system sends the AC signals over S1 and S2. Simultaneously, on the detecting satellite, a receiving electrode detects the voltage. In one embodiment, an integral circuit on the detecting satellite performs an integral operation on the detected voltage. After the transmission from the broadcasting satellite is complete, the system allows the detecting satellite to communicate the integral results to a data analysis mechanism. The system facilitates both transmission and signal collection over S1 and S2.

In one embodiment, the system uses a 100 KHz AC signal to establish the AC electric field. A lock-in amplification circuit included on the detecting satellite detects the induced voltage on the receiving electrode. In a further embodiment, one of the transmitting electrodes is coupled to the ground through one wire, for example, S1. The system compares the integral result obtained from the voltage induced on the detecting electrode with a reference value to determine the amount and the direction of the bending.

In a further embodiment, the system performs the aforementioned operations repetitively with short intervals to detect the motions of the heart. Furthermore, the system can select different broadcasting satellites along the lead and measure the induced potential at the respective neighboring satellites to map out a contour of the pacing lead.

Figure 4:
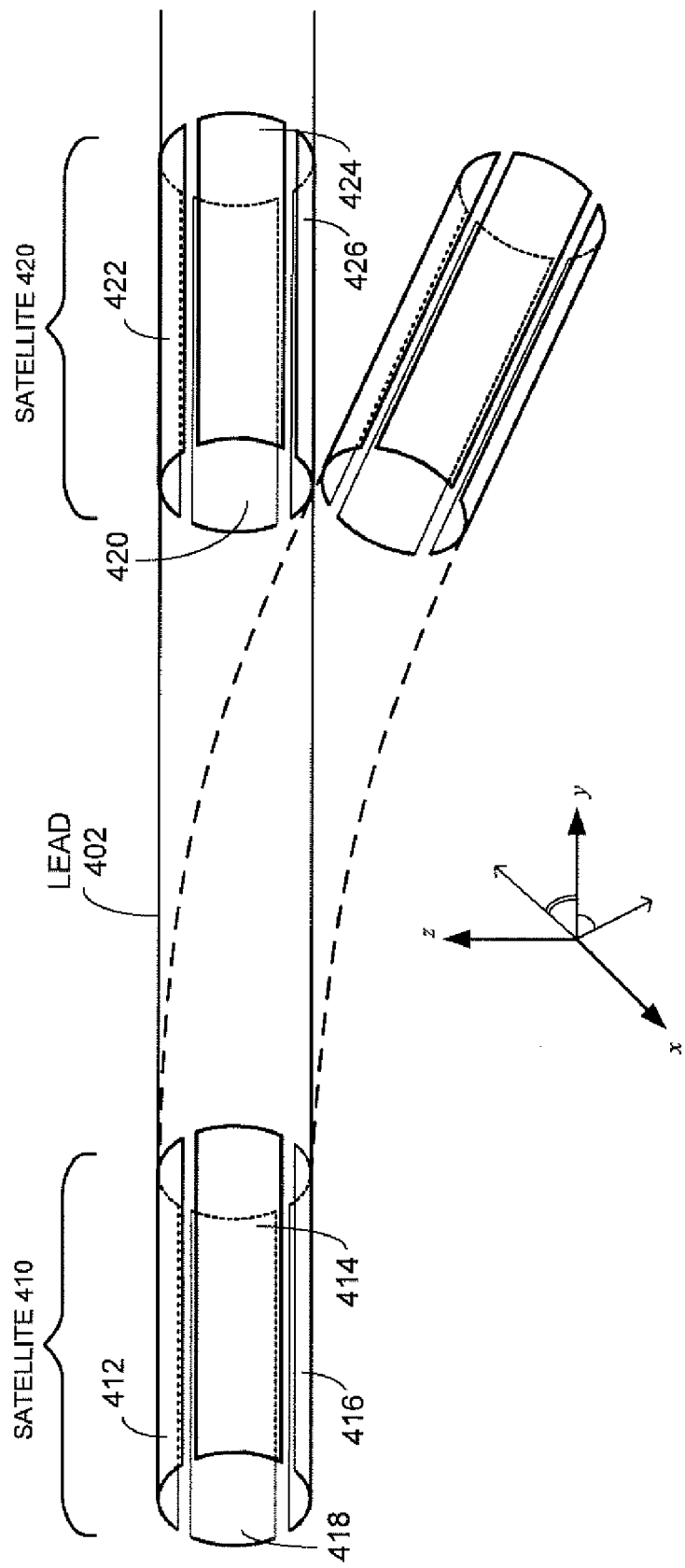
FIG. 4 illustrates an example where the system measures the bending between two satellites operating as electrical angle gauges in accordance with an embodiment of the present invention.

FIG. 4 illustrates an example where the system measures the bending between two satellites operating as electrical angle gauges in accordance with an embodiment of the present invention. The system selects a satellite 410 to broadcast the AC signals. Satellite 410 includes four electrodes, 412, 414, 416, and 418, in four quadrants, respectively. The system transmits the AC signals through electrodes 412 and 416 and establishes an AC electric field extending to a neighboring satellite 420, which includes electrodes 420, 422, 424, and 426. The system can select one of the electrodes, for example, electrode 424, to detect the induced voltage.

During operation, the system first transmits the AC signals through electrodes 412 and 416. Correspondingly, electrode 424 detects an induced voltage, which is integrated by an integral circuit within satellite 420. The system continues transmitting the AC signals for a period of time to allow the integral circuit on satellite 420 to accumulate sufficient charge. Subsequently, the system discontinues the transmission to allow satellite 420 to communicate the integral result to a data-analysis mechanism. The integral result is then compared with a reference value to determine the amount of bending satellite 420 experiences with regard to satellite 410.

By transmitting through different broadcasting electrodes, the system can determine the direction of bending. In this example, the system transmits the AC signals through electrodes 412 and 416. Consequently, the system can determine the amount of bending, represented by the deflection angle θ, of lead 402 in the y-z plane, which is parallel to the paper plane. Alternatively, the system can transmit through electrodes 414 and 418 to determine the amount of bending, represented by the deflection angle γ, of lead 402 in the x-y plane, which is orthogonal to the paper plane.

Figure 5:
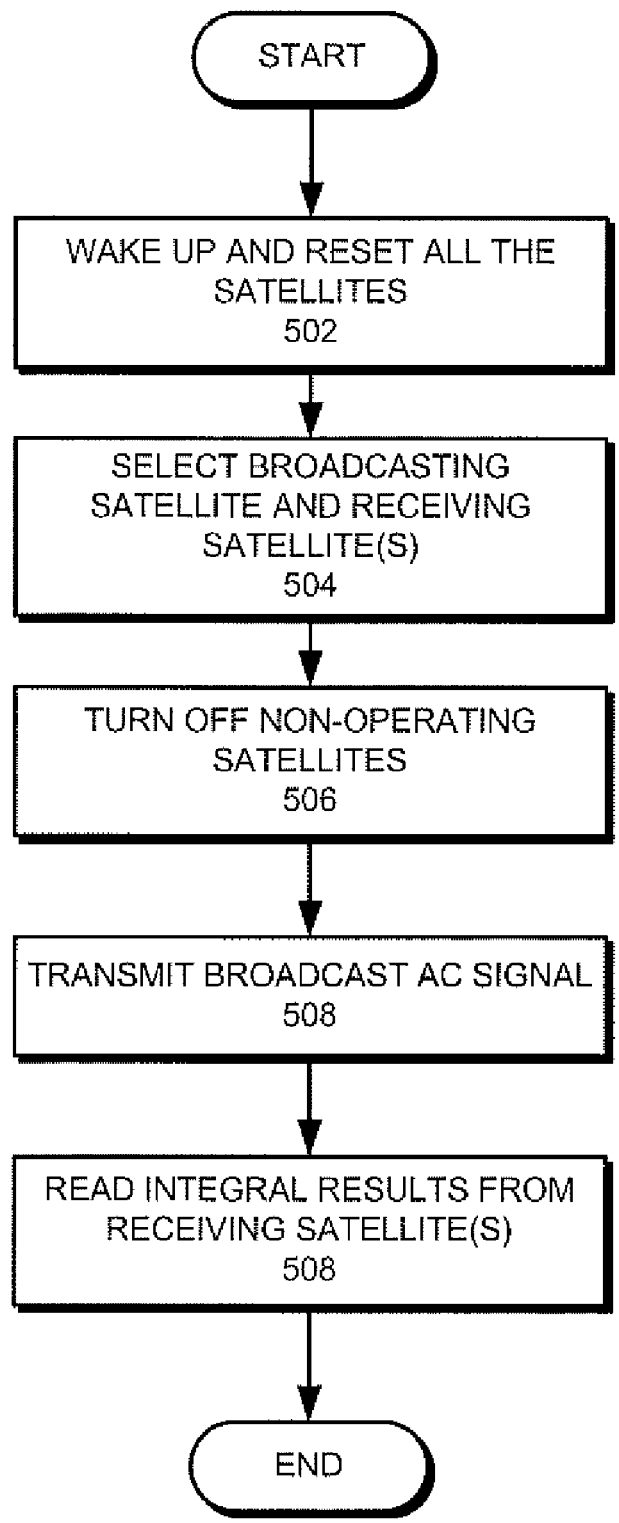
FIG. 5 presents a flow chart illustrating an exemplary cycle of measuring cardiac motions using electrical angle gauges in accordance with an embodiment of the present invention.

FIG. 5 presents a flow chart illustrating an exemplary cycle of measuring cardiac motions using electrical angle gauges in accordance with an embodiment of the present invention. During a transmission-detection cycle, the system starts by waking up and resetting all the satellites (step 502). The system then selects the broadcasting satellite and the receiving satellite(s) (step 504). The system also specifies the operative electrodes on the broadcasting satellite and the receiving satellite. Furthermore, the system may select multiple receiving satellites to measure bending at multiple locations.

Next, the system issues commands to turn off non-operating satellites (step 506). The system then transmits the broadcast AC signal to the broadcasting satellite (step 508). After transmitting for a period of time, the system discontinues the broadcast and reads the integral results from the receiving satellites (step 508).

A further embodiment of the present invention uses the implanted satellite as a transmission source and measures the induced voltages through electrodes placed outside a patient's body. During operation, the system transmits an AC signal through a pair of electrodes on one implanted satellite, or two electrodes from two different satellites. The transmission establishes an AC electric field which extends to the space surrounding the patient's body. A number of detecting electrodes are placed on the surface of the patient's body to detect the electric field. Hence, with the aid of data-collection and analysis instruments, a physician can determine the location and orientation of the transmitter satellite according to the distribution of the detected electric field. In addition, the transmission, signal detection, and data analysis can be performed continuously and simultaneously, which allows the physician to observe the cardiac motion in real time. Furthermore, by locating multiple satellites along a pacing lead, the physician can determine the location and position of the lead.

Embodiments of the present invention may also be used for orthopedic procedures, wherein the electric angle gauges can detect how bones are bending or stretching. The advantage herein is that a physician can place a single lead that runs along the length of a leg and measures various parameters. In other applications, embodiments of the present invention can be placed in facial bones for plastic surgical purposes which allow observation of changes in dimension over time.

In further applications, embodiments of the present invention can be used for spinal surgery to assist examination of fused parts of the spine and to detect residual motion between fused parts in which case the fusing has to be redone. Additional applications of embodiments of the present invention include use of the electric angle gauges within or in the vicinity of organs such as bladders, lungs, and stomachs. By placing multiple electric angle gauges around the periphery of these organs, a physician can determine the change in the sizes of these organs.

Summarizing aspects of the above description, in using the systems of the invention, such methods include implanting a system, e.g., as described above, into a subject; and then employing the system to obtain motion data. The description of the present invention is provided herein in certain instances with reference to a subject or patient. As used herein, the terms "subject" and "patient" refer to a living entity such as an animal. In certain embodiments, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects, e.g., patients, are humans.

Computer Readable Medium

One or more aspects of the subject invention may be in the form of computer readable media having programming stored thereon for implementing the subject methods. The computer readable media may be, for example, in the form of a computer disk or CD, a floppy disc, a magnetic "hard card", a server, or any other computer readable media capable of containing data or the like, stored electronically, magnetically, optically or by other means. Accordingly, stored programming embodying steps for carrying-out the subject methods may be transferred or communicated to a processor, e.g., by using a computer network, server, or other interface connection, e.g., the Internet, or other relay means. More specifically, computer readable medium may include stored programming embodying an algorithm for carrying out the subject methods. Accordingly, such a stored algorithm is configured to, or is otherwise capable of, practicing the subject methods, e.g., by operating an implantable medical device to perform the subject methods. The subject algorithm and associated processor may also be capable of implementing the appropriate adjustment(s). Of particular interest in certain embodiments are systems loaded with such computer readable mediums such that the systems are configured to practice the subject methods.

Use of the systems may include visualization of data obtained with the devices. Some of the present inventors have developed a variety of display and software tools to coordinate multiple sources of sensor information which will be gathered by use of the inventive systems. Examples of these can be seen in international PCT application serial no. PCT/US2006/012246 entitled Automated Optimization of Multi-Electrode Pacing for Cardiac Resynchronization; the disclosure of which application, as well as the priority applications thereof are incorporated in their entirety by reference herein.

Kits

Also provided are kits that include the implantable devices or systems, such as an implantable pulse generator, e.g., as reviewed above. In certain embodiments, the kits further include at least a control unit, e.g., in the form of a pacemaker can. In certain of these embodiments, the structure and control unit may be electrically coupled by an elongated conductive member. In certain embodiments of the subject kits, the kits will further include instructions for using the subject devices or elements for obtaining the same (e.g., a website URL directing the user to a webpage which provides the instructions), where these instructions are typically printed on a substrate, which substrate may be one or more of; a package insert, the packaging, reagent containers and the like. In the subject kits, the one or more components are present in the same or different containers, as may be convenient or desirable.

The following examples are offered by way of illustration and not by way of limitation.

EXPERIMENTAL

Figure 2B:
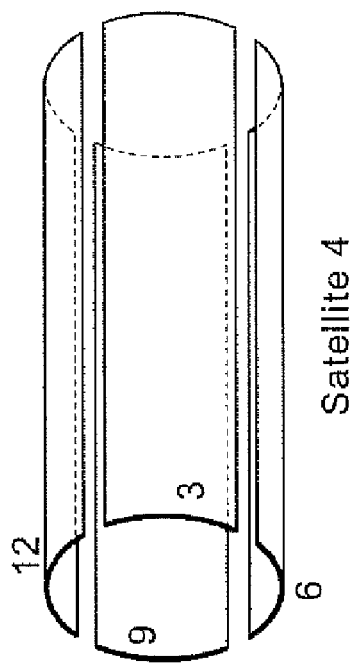
FIGS. 2B and 2C provide views showing electrode configuration and mode of operation in accordance with an embodiment of the present invention.
Figure 2B:
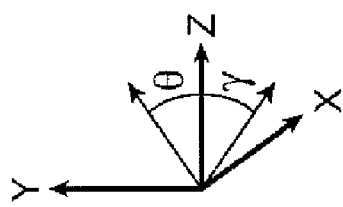
Figure 2B:
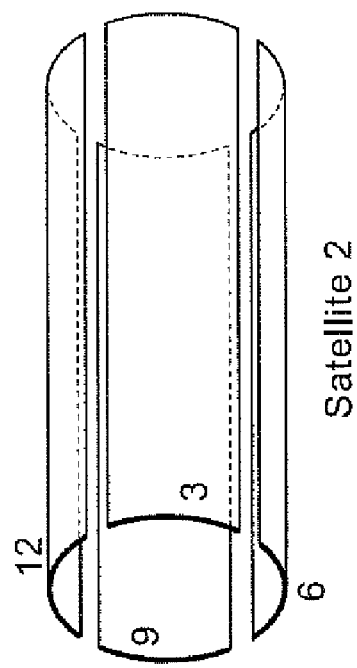
Figure 2C:
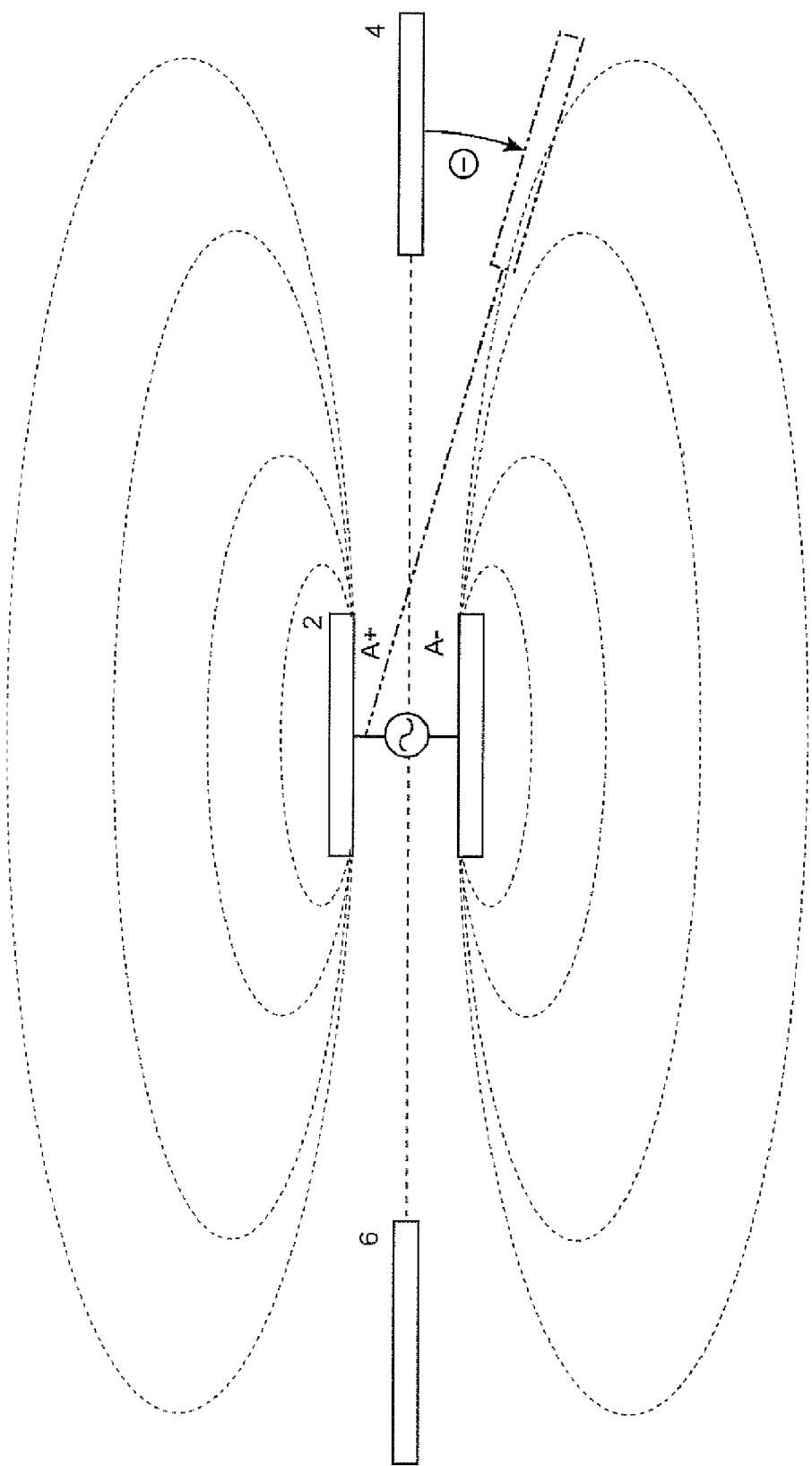

In one application of the present electrical angle gauge invention, the innovation of the invention allows the measurement of the relative position of various electrodes on a multiple-electrode lead. The positions that are obtainable may be assigned notations similar to the face of a clock at twelve, three, six and nine o'clock. In FIGS. 2B and 2C, views are provided showing two of those electrodes, such as at twelve o'clock and six o'clock on the middle satellite. At one of the neighboring satellites, one or two of the electrodes at the three or nine o'clock positions are selected. In some cases, the average of those two numbers is provided.

To provide the information to obtain clinical data, the relative angle or displacement of the neighboring electrodes is measured with respect to the center electrodes. This allows determination of the location of their position in three dimensional space. As shown, the twelve o'clock and six o'clock electrodes on satellite 2 are stimulated with an AC signal. When the nearby electrode in satellite 4 is exactly lined up with satellite 2 there is no angle detected between the two. That is, the angle theta shown in the drawing is zero. In this position, the signal will be exactly half of the amplitude of the voltage expressed across the two electrodes.

As the electrode moves down, the amplitude will be closer to the minus A field as shown in FIG. 2C, while as the electrode moves up, the amplitude will move closer to the plus A field. The modification in the amplitude corresponding to relative electrode movement allows the correlation between angle and the theta. The theta is the correlation between the voltage, the amplitude of the ac voltage and theta where theta is the angle between the center electrode and the neighboring electrode.

Employing the other two electrodes of satellite 2, that is the three and six o'clock electrodes, to broadcast an AC field provides additional opportunities to obtain useful clinical data. Either using time multiplexing of the same frequency or frequency multiplexing of a different frequency is useful. Subsequently, using the opposite electrodes on satellites 4 and 6 provides the average of the twelve and six electrodes. From this data is calculated the angle gamma, which is the angle in the orthogonal direction. Similarly, the angle gamma can be obtained, and is related to the amplitude of the received signal.

Also shown in FIG. 2C are the field lines that are typically propagated by a bipolar electrode in a conductive environment. If the angle crosses down, it crosses into one of those isopotential lines. This increases its value, and its potential becomes closer to the electrode below. In practice, the various satellites would be employed in turn. This, if eight different satellites are employed, six inner satellites would take a turn at broadcasting. That is, the nearby ones would be receiving the signals. From this data would be sent out to a local computer. This computer would compute what all of the various angles are. As the distances between the satellite are fixed and known, a determination of the precise relative location of all these satellites is available.

From that information, knowing relative location of the satellites, a synchrony index is computed. By example, knowing which satellites are closest to the right ventricle and when and at what time are they moving, these satellites provide information that can be employed in determining a synchrony index. Using position information so obtained, an estimate of the volume of the heart and ejection factors and other human dynamic parameters of interest to clinicians may be calculated.

There are a variety of approaches to obtaining data based on the teachings of the present invention. In an alternate embodiment, instead of broadcasting a fixed amplitude from the inner satellite and looking at the amplitude modulation of the neighboring satellites, the distant electrodes can be utilized as well. For instance, the amplitude of the first two satellites are modulated to maintain a constant, null signal in the neighboring one. Then, the relative values of the broadcasting ones are actually related to theta as opposed to received signal.

This alternate embodiment is best practiced in a closed loop between the two satellites. For that approach, the theta is related to the amplitude of the broadcast signal, and the received signal remains some constant value. The broadcaster is modulated in such a way to keep the receiver constant. Alternately, the broadcaster is kept constant, and the modulated signal on the receiver is obtained, producing a measurement of theta.

FIG. 2B shows two neighboring satellites. Satellite 2 is the broadcasting satellite and satellite 4 on the right is the receive satellite. Alternately, the converse arrangement will also function, where satellite 4 becomes the broadcast satellite and satellite 2 becomes the receive satellite. Again, the four electrodes are at twelve, three, six, and nine according to the locations of the clock. When broadcasting occurs between electrodes six and twelve on satellite two, the average of the signals received on satellite 4, electrodes 3 and 9 can be used to provide the angle in the direction vertical from six and twelve.

The axis between six and twelve is designated as the y-axis. The axis that goes from three and nine is designated as the x-axis. The axis that goes between the two satellites longitudinally of the lead is designated as a z-axis. By driving the voltage between six and twelve on satellite two, the potential is measured between three and nine on satellite four, thus measuring theta. Theta is an angle in the z-y plane. When driving satellite 2 between electrodes 3 and 9, the average of electrodes six and twelve on satellite six and four are measured. In this case, the angle gamma is measured, which is in the x-z plane, The two orthogonal angles are measured, which is the theta, of the orientation of satellite four. This is with respect to satellite 2, in the x-z plane and y-z plane, where z is along the axis of the lead. Using this method, the relative position in the x-z and y-z plane on satellite four with respect to satellite two is generated. The distance between the two is fixed because they are firmly attached to the lead. From these two angles one can compute with a fair amount of accuracy the actual locations of the satellites.

Additional sensors with various designs have been described in a number of applications by some of the present inventors. These sensors can be used jointly with the present inventive system. In addition, these applications also describe multiplexing systems previously developed by some of the present inventors with which embodiments of the present invention are employed. This prior work by some of the present inventors describes the use of strain gauges for resynchronization. One system is described in part in U.S. Patent Application No. 60/638,247 entitled "Cardiac Motion Characterization by Strain Measurement" by some of the present inventors, filed Dec. 20, 2004. An additional system is described in U.S. Patent Application No. 60/667,749 entitled "Cardiac Motion Detection Using Fiberoptic Strain Gauges", by some of the present inventors, filed Mar. 31, 2005.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for obtaining motion data for a physiological location of a body, the method comprising:
    producing an electric field from a pair of broadcasting electrodes in a first satellite structure formed on a pacing lead, wherein the pacing lead is implanted in a body;
    detecting a change in an electric potential of a receiving electrode in a second satellite structure formed on the pacing lead in response to a movement of the pacing lead, wherein the electric potential of the receiving electrode is induced by the electric field, and wherein the receiving electrode is attached to a physiological location of the body;
    determining an angle by which the receiving electrode deflects from a mid-potential plane between the pair of broadcasting electrodes by processing the change in the electric potential of the receiving electrode; and
    generating motion data for the physiological location of the body based on the angle by which the receiving electrode deflects from the mid-potential plane.

2. The method according to claim 1, wherein the physiological location is a cardiac location and the motion data are cardiac motion data.

3. The method according to claim 1, wherein the electric field is an alternating current electric field.

4. The method according to claim 1, wherein each of the first satellite structure and the second satellite structure includes a control chip.

5. The method according to claim 1, wherein each of the first satellite structure and the second satellite structure is a segmented satellite structure.

6. The method according to claim 1, wherein the first satellite structure is a quadrant electrode structure and the pair of broadcasting electrodes are opposing electrodes of the quadrant electrode structure.

7. The method according to claim 1, wherein the pacing lead is a multiplex lead.

8. The method according to claim 7, wherein the multiplex lead includes a two-wire bus and the satellite electrode structures are electrically coupled to the two-wire bus.

9. The method according to claim 1, wherein the motion data comprises timing data.

10. The method according to claim 1, further comprising administering an electrical pulse to a tissue of the body based on the motion data.

11. The method according to claim 1, wherein the body is a human body.

12. The method according to claim 1, wherein the producing the electric field comprises transmitting an alternating current through the pair of broadcasting electrodes.

13. A system for obtaining motion data for a physiological location of a body, the system comprising:
    (a) a lead having a first segmented electrode satellite structure and a second segmented electrode satellite structure;
    (b) a processing element communicatively coupled to the lead and configured to:
        (i) select the first segmented electrode satellite structure as a broadcasting satellite and the second segmented electrode satellite structure as a receiving satellite, wherein the broadcasting satellite comprises a pair of broadcasting electrodes;
        (ii) produce an electric field from the broadcasting satellite;
        (iii) detect a change in an electric potential on a receiving electrode of the receiving satellite in response to a movement of the lead, wherein the electric potential of the receiving electrode is induced by the electric field, and wherein the receiving electrode is attached to a physiological location of a body;
        (iv) determine an angle by which the receiving electrode deflects from a mid-potential plane between the pair of broadcasting electrodes by processing the change in the electric potential of the receiving electrode; and
        (v) generate motion data for the physiological location of the body based on the angle by which the receiving electrode deflects from the mid-potential plane.

14. The system according to claim 13, wherein the broadcasting satellite comprises a pair of electrodes.

15. The system according to claim 13, wherein the receiving satellite comprises at least one electrode.

16. The system according to claim 13, wherein each one of the first segmented electrode satellite structure and the second segmented electrode satellite structure is a quadrant electrode structure.

17. A nontransitory computer readable storage medium having a processing program stored thereon, wherein the processing program is configured to operate a system comprising a pacing lead with a pair of broadcasting electrodes and with a receiving electrode to perform a method for obtaining motion data for a physiological location of a body, the method comprising:
    producing an electric field from the pair of broadcasting electrodes on the pacing lead, wherein the pacing lead is implanted in a body;

detecting a change in an electric potential of the receiving electrode in response to a movement of the pacing lead, wherein the electric potential of the receiving electrode is induced by the electric field, and wherein the receiving electrode is attached to the physiological location of the body;

determining an angle by which the receiving electrode deflects from a mid-potential plane between the pair of broadcasting electrodes by processing the change in the electric potential of the receiving electrode; and generating the motion data for the physiological location of the body based on the angle by which the receiving electrode deflects from the mid-potential plane.

* * * * *